(12) United States Patent
Wholey et al.

(10) Patent No.: US 6,652,554 B1
(45) Date of Patent: Nov. 25, 2003

(54) INSTRUMENT FOR THROMBOEMBOLIC PROTECTION

(76) Inventors: Mark H. Wholey, 816 Woodland Ave., Oakmont, PA (US) 15139; Michael Wholey, 19407 Straus, San Antonio, TX (US) 78256

( * ) Notice: Subject to any disclaimer, the term of this patent is extended or adjusted under 35 U.S.C. 154(b) by 0 days.

(21) Appl. No.: 09/476,829

(22) Filed: Jan. 3, 2000

Related U.S. Application Data (60) Provisional application No. 60/114,627, filed on Jan. 4, 1999.

(51) Int. Cl.[7] .............................................. A61M 29/00
(52) U.S. Cl. ...................................... 606/200; 604/104
(58) Field of Search ....................... 606/113–114, 127, 606/200, 108, 110, 128; 600/434, 585, 433, 435, 462, 466–469; 604/96.01, 93.01, 915, 104–107, 523, 528

(56) References Cited

U.S. PATENT DOCUMENTS

| | | |
|---|---|---|
| 2,854,983 A | 10/1958 | Mobin-Uddin |
| 3,540,431 A | 11/1970 | Mobin-Uddin |
| 3,692,029 A | 9/1972 | Adair |
| 3,952,747 A | 4/1976 | Kimmell, Jr. |
| 4,403,612 A | 9/1983 | Fogarty |
| 4,425,908 A | 1/1984 | Simon |
| 4,493,711 A | 1/1985 | Chin et al. |
| 4,512,762 A | 4/1985 | Spears |
| 4,564,014 A | 1/1986 | Fogarty et al. |
| 4,619,246 A | 10/1986 | Molgaard-Nielsen et al. |
| 4,723,549 A | 2/1988 | Wholey et al. |
| 4,811,743 A | * 3/1989 | Stevens |
| 4,873,978 A | 10/1989 | Ginsburg |
| 4,969,891 A | 11/1990 | Gewertz |
| 5,011,488 A | 4/1991 | Ginsburg |
| 5,053,008 A | * 10/1991 | Bajaj ........................... 604/104 |
| 5,102,415 A | 4/1992 | Guenther et al. |
| 5,344,427 A | 9/1994 | Cottenceau et al. |
| 5,549,626 A | 8/1996 | Miller et al. |
| 5,695,511 A | 12/1997 | Cano et al. |
| 5,709,704 A | 1/1998 | Nott et al. |
| 5,769,816 A | 6/1998 | Barbut et al. |
| 5,779,716 A | 7/1998 | Cano et al. |
| 5,814,064 A | 9/1998 | Daniel et al. |
| 5,827,324 A | 10/1998 | Cassell et al. |
| 5,836,968 A | 11/1998 | Simon et al. |
| 5,836,969 A | 11/1998 | Kim et al. |
| 5,846,260 A | 12/1998 | Maahs |
| 5,853,420 A | 12/1998 | Chevillon et al. |
| 5,910,154 A | * 6/1999 | Tsugita et al. ............... 606/200 |

FOREIGN PATENT DOCUMENTS

WO    WO 96/01591    *  1/1996

OTHER PUBLICATIONS

"Case Study Presentations: Visual and Histological Evidence of Particulate Emboli Captured with the EMBOL X Arterial Filter During Cardiac Surgery," *Arterial Cannula and Filter System*, 2 pp., Sep. 1998.

* cited by examiner

*Primary Examiner*—LoAn H. Thanh
(74) *Attorney, Agent, or Firm*—Alan G. Towner, Esq.; Pietragallo, Bosick & Gordon (57) ABSTRACT

A thromboembolic capturing system captures thromboemboli in the arterial and venous circulation. A vascular tube such as a guidewire includes a porous filter at is distal end. The filter is collapsible, capable of maintaining open and closed configurations when placed within a vessel. Opening and closing of the filter is controlled by strings or sutures running through the tube. The filter is able to retain captured thromboembolic material in conjunction with angioplasty or interventional cardiovascular procedure. When the tube comprises a guidewire, it is of sufficient strength, torquability and softness to be used for angioplasty, stent placement and other interventional procedures.

25 Claims, 6 Drawing Sheets

INSTRUMENT FOR THROMBOEMBOLIC PROTECTION

CROSS REFERENCE TO RELATED APPLICATION

This application claims the benefit of U.S. Provisional Patent Application Serial No. 60/114,627 filed Jan. 4, 1999, which is incorporated herein by reference.

FIELD OF THE INVENTION

The present invention relates to thromboembolic protection, and more particularly relates to an instrument including a collapsible filter mounted on a tube such as a guidewire for thromboembolic protection.

BACKGROUND INFORMATION

It is common practice today to open occluded (i.e., blocked) or stenotic (i.e., narrowed) blood vessels by inserting a guidewire and then a catheter carrying a balloon shaped distal end, and inflating the balloon, which exerts radial force, to press the stenosis outward against the wall of the vessel. This procedure is called balloon angioplasty. Frequently, an implantable metallic stent will be used additionally to provide greater radial strength and longer-term patency. The stent can be delivered with a balloon catheter or on a special sheath. This procedure is called A stent placement.

During balloon angioplasty and stent placement of the stenotic lesion, there is the risk of dislodging fragments of plaque, thrombus (blood clots) or other material. If the lesion involves arterial circulation, then the particles could flow into smaller vessels in the brain, other organs or extremities resulting in disastrous complications. Likewise, if the lesions involve the venous circulation, then the thromboemboli could flow into the heart and lung possibly resulting in the demise of the patient.

There have been various devices and equipment to deal with stenotic lesions. As described, angioplasty and stents have been used to radially expand the lesion into the wall of the vessel. But these instruments can accidentally dislodge plaque and thrombus. Atherectomy devices are used to cut the plaque but have poor clinical results in actually treating the lesion and do not effectively trap thromboemboli.

Various patents have recently addressed th e subject with the use of balloons or straining devices. However, such designs do not effectively trap particles or are too traumatic in crossing high grade stenoses. The present invention provides these capabilities, in addition to providing a guidewire which can be used to deliver catheters and stents to treat the lesion.

SUMMARY OF THE INVENTION

This invention relates to an apparatus and method for collecting blood clots, pieces of plaque and other material that may be accidentally dislodged during interventional procedures in the human vasculature, such as arterial and venous angioplasty and stent placement. The apparatus includes a collapsible filter, which allows the dislodged fragments and thromboemboli to be captured and removed from the body. The filter is porous in order to allow red blood cells and other normal blood products to pass while the filter is open.

In one embodiment of the invention, the apparatus also serves a dual purpose as a guidewire. Once the distal end of the apparatus is advanced past the stenosis or targeted narrowing of the vessel, the operator may use the apparatus to advance various coaxial catheters and devices into position to treat the lesion. Balloon catheters, stent delivery systems, intravascular ultrasound catheters and other interventional systems can be advanced over the present apparatus.

An aspect of the present invention is to provide such a filter device carried by a tube such as a guidewire which is inserted into the occluded or stenotic vessel in a retracted position, and can be easily and remotely opened allowing effective trapping of thromboembolic material.

Another aspect of the invention is to provide a guidewire to be advanced past the targeted lesion. Afterwards, the apparatus will have the needed characteristics to provide support for advancement of coaxial catheters such as balloon catheters and stent delivery systems to the lesion site for treatment.

A further aspect of the invention is to provide such a guidewire with a filter, which securely retains thromboembolic fragments of the stenosis when the filter is retracted for removal from the blood vessel.

Another aspect of the invention is to provide such a guidewire with an extendable and retractable filter, minimizing trauma to the vessel as the guidewire is advanced and withdrawn to and past the lesion.

A further aspect of the invention is to achieve the foregoing aspects with minimum interruption of blood flow through the vessel.

These and other aspects of the present invention will be more apparent from the following description.

BRIEF DESCRIPTION OF THE DRAWINGS

FIGS. 6a and 6b are longitudinal sectional views of the proximal end or hub of the apparatus of FIG. 1. FIG. 6a shows the apparatus in the retracted position, while FIG. 6b shows the apparatus in the extended position.

DETAILED DESCRIPTION

The apparatus of the present invention includes a flexible tube with a collapsible filter attached to the end of the tube. The filter is extendable outward toward the interior wall of the blood vessel of a patient to trap fragments of stenosis broken loose by intervention at a lesion site. The filter is retractable along the tube to retain the trapped fragments while the tube is withdrawn from the blood vessel. In one embodiment, the tube comprises a guidewire. Alternatively, the tube may be any other suitable flexible hollow member, such as a catheter.

In the exemplary embodiment described herein, the filter includes a plurality of ribs attached near the distal end of the tube angularly placed around the tube. In the closed position, the ribs extend along the tube from its distal toward its proximal end. The ribs are preferably made of a flexible or memory metal resulting in the outward expansion of the ribs and porous filter. Filter material bridges the gaps between the ribs to form a cup-shaped trap. The filter material is composed of any suitable porous material which sufficiently allows normal blood flow to pass. For example, the filter may be made of porous fabric, plastic such as PTFE or metal.

In a preferred form of the invention, the ends of the ribs are secured with control strings, such as wires, sutures or suture-like materials, which enter and run at least partially through the hollow tube. The control strings are secured, either directly or by an intermediate member, to an actuator device in the hub or proximal end of the tube. When the actuator device at the proximal end of the tube is pushed forward in a linear direction, the control strings are relaxed resulting in outward expansion of the ribs and filter against the vessel wall.

When the procedure is completed and particles and thromboembolic fragments have collected in the filter, the filter and ribs are retracted against the exterior tube wall. This is achieved by pulling the actuator device in a linear direction, which applies tension to the control strings, resulting in retraction of the ribs and filter against the outer wall of the tube. The control strings are preferably aligned and are preferably made of a composition such as suture material which prevents them from crossing each other and becoming tangled. The control strings may extend the entire distance from the ribs to the actuator device. Alternatively, the sutures may be attached to an intermediate member such as a flexible sliding rod or sleeve which, in turn, is connected to the actuator device.

In a preferred embodiment, the present apparatus may also serve as a guidewire which allows the operator to coaxially advance various instruments and catheters, such as balloon catheters and stent systems, to the site of the lesion for particular treatment.

As shown in the embodiment of FIGS. 1–6, the device of the present invention includes a flexible guidewire 1 which is inserted into a blood vessel 2 narrowed by a stenosis through an incision (not shown) upstream of the stenosis. Although a guidewire is shown in this embodiment, other flexible tubing may be used. The tube or guidewire preferably has an outer diameter of greater than 0.02 inch and less than 0.1 inch. For example, the guidewire 1 may have an outer diameter of 0.035 inch and an inner diameter of 0.022 inch.

Figure 1:
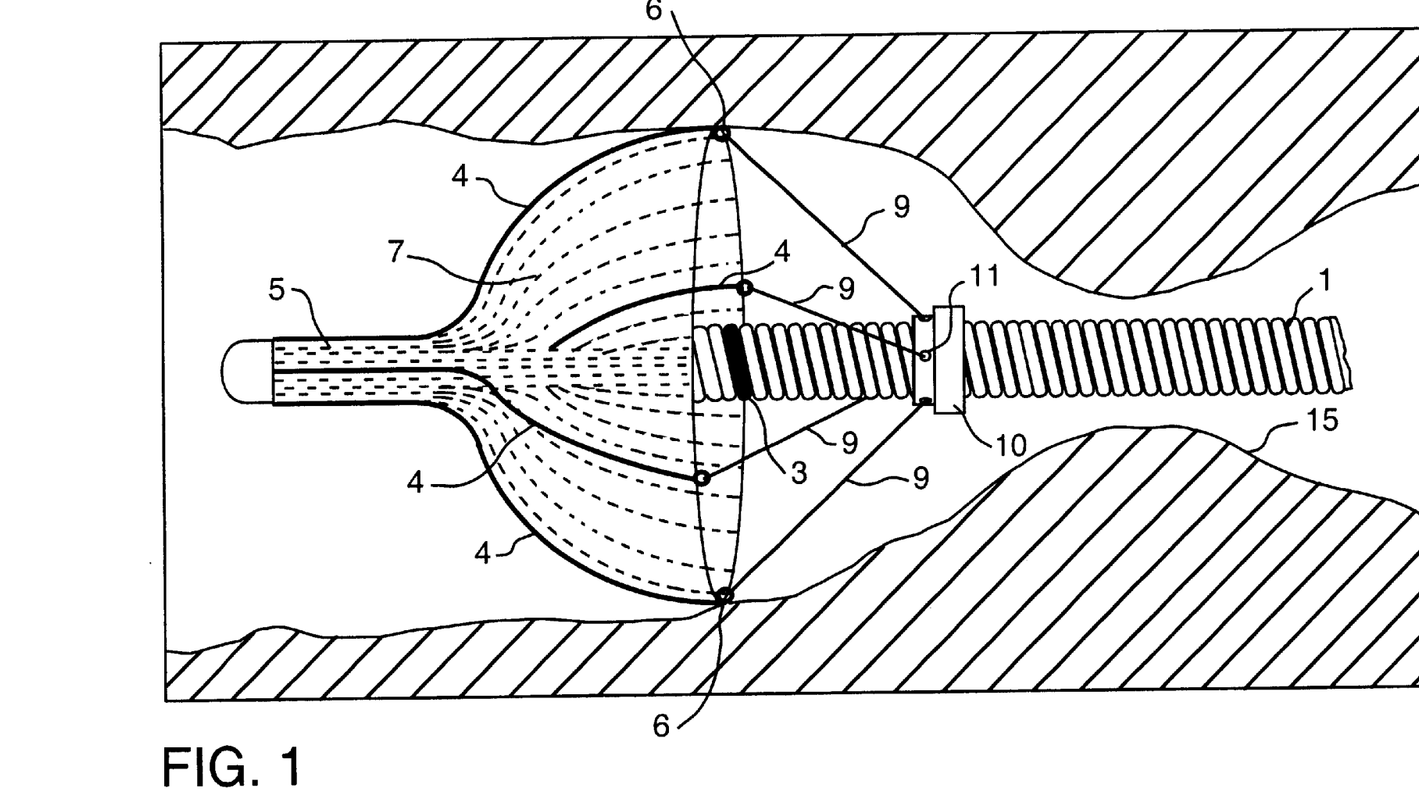
FIG. 1 is a partially schematic longitudinal side view of a filter-equipped guidewire in accordance with an embodiment of the invention, which is placed adjacent a stenosis in a blood vessel with the filter in an extended position.

The guidewire 1 may be advanced through the lumen of a catheter (not shown) past the lesion into position with its distal end downstream of the stenosis. Angiography may be used as a known aid in positioning the catheter. Along the shaft of the guidewire 1, at least one of the coils 3 may be coated or constructed with a material of higher atomic density to allow demarcation of the filter position under fluoroscopy. This will assist in positioning the guidewire 1 along the vessel 2.

Figure 4:
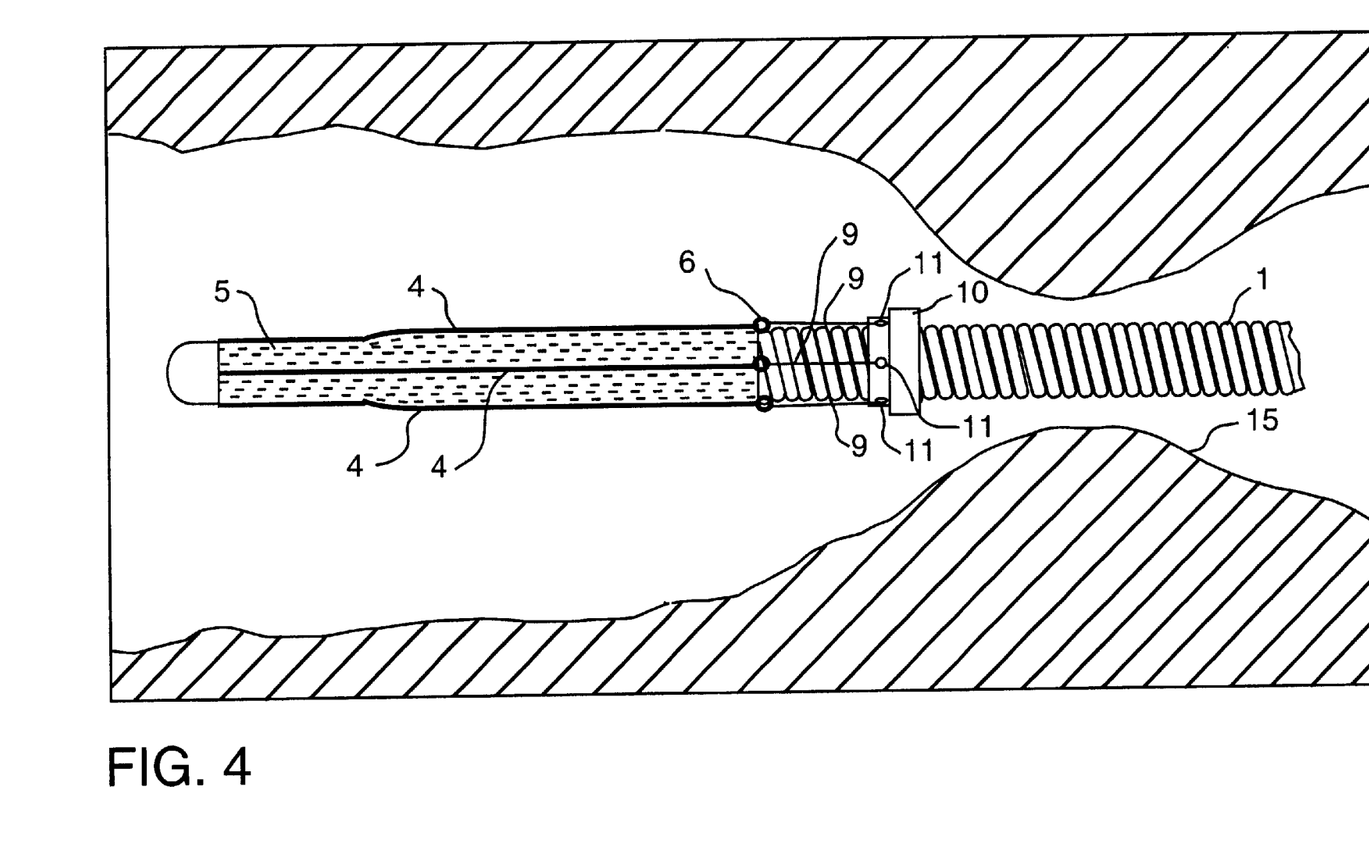
FIG. 4 is a longitudinal side view of the apparatus of FIG. 1, with the filter in a retracted position.
Figure 5:
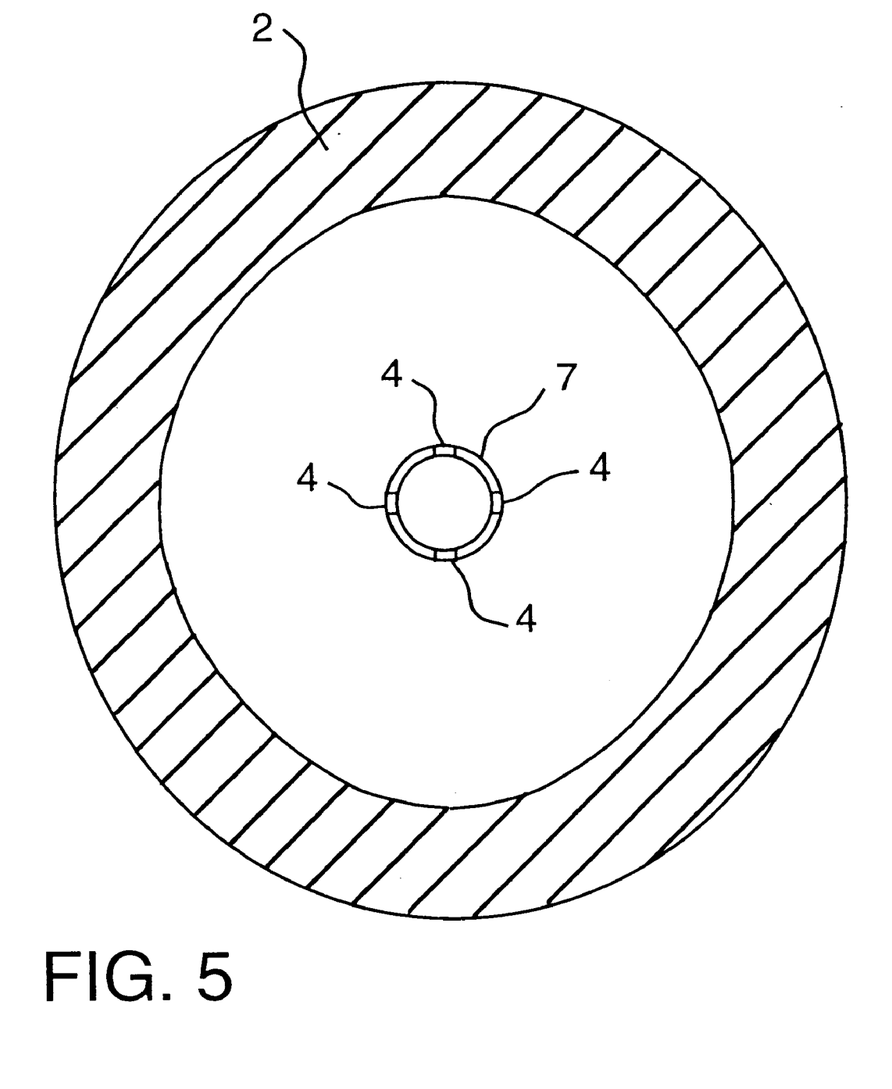
FIG. 5 is an end view of the retracted filter of FIG. 4.

A filter device is affixed to the guidewire shaft near the distal end. The filter device includes a plurality of ribs 4, of which four are shown in the embodiment illustrated, equiangularly spaced around the external circumference of the guidewire 1. More or less ribs may be used. For example, a device with six equiangularly ribs may be constructed. The distal ends 5 of the ribs 4 are secured to the shaft of the guidewire 1, such as by an adhesive, solder or outer sleeve. When the ribs 4 are in the retracted position, they may extend in a substantially straight line along the axis of the guidewire 1, as shown in FIG. 4. Alternatively, the retracted ribs may extend axially along the guidewire 1 in any other suitable configuration, such as spirals or the like.

The ribs 4 are preferably formed of a resilient material, e.g., stainless steel, Nitinol memory metal or plastic, which is prestressed or preformed resulting in an expansible or outward bias. The tips 6 of the ribs 4 are preferably curved inward to minimize trauma to the vessel wall.

A filter material 7 spans the gaps between and is secured to the ribs 4. The filter material 7 may be attached to the ribs by any suitable means such as sutures, pockets, adhesives and the like. In one embodiment, the filter material 7 may be tied to the ribs 4 by sutures which also act as the control strings of the apparatus. A wire or other type of support member (not shown) may be attached at or near the outer circumference of the filter material and/or between the ribs 4 in order to provide added support.

Figure 2:
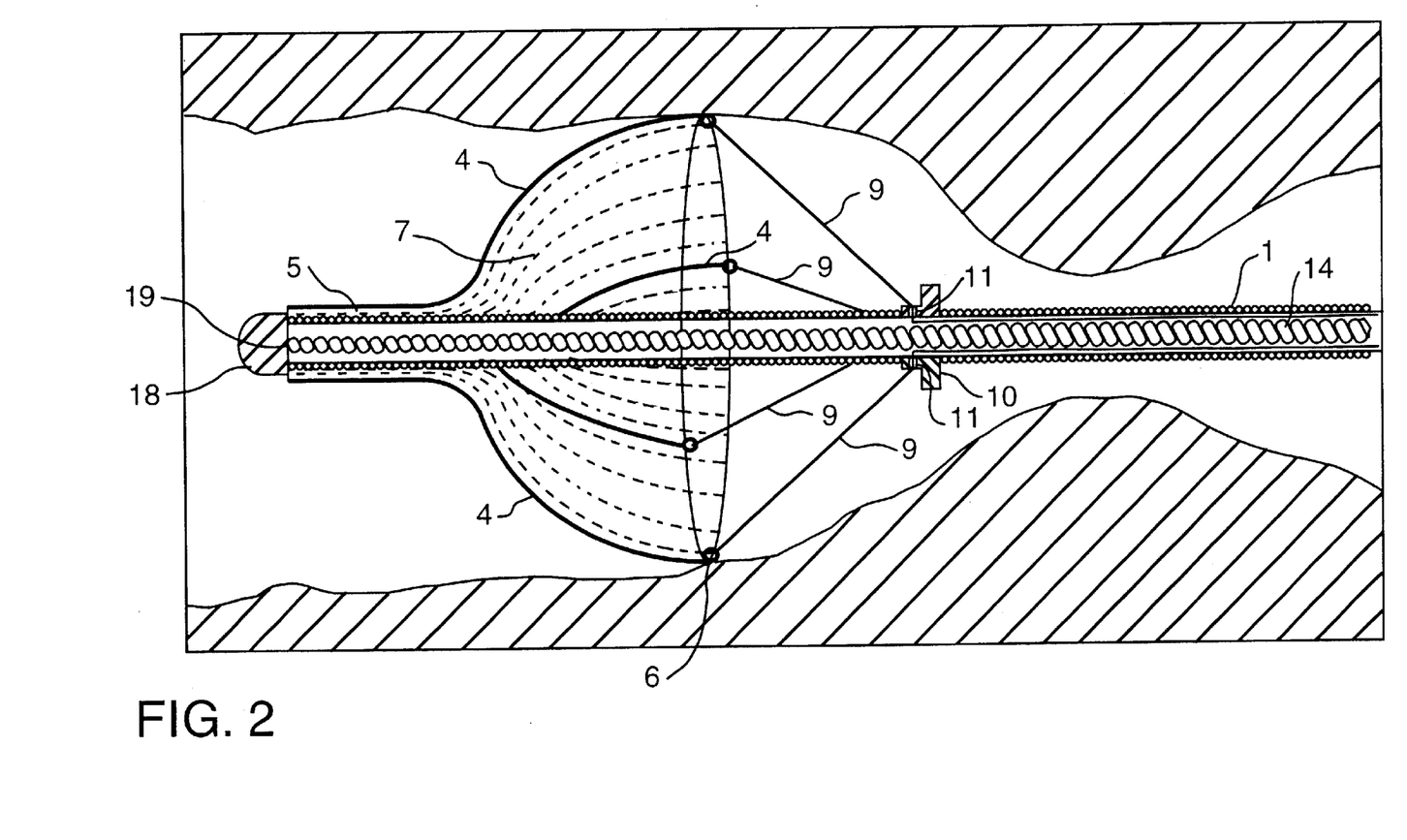
FIG. 2 is a longitudinal sectional view of the apparatus of FIG. 1.
Figure 3:
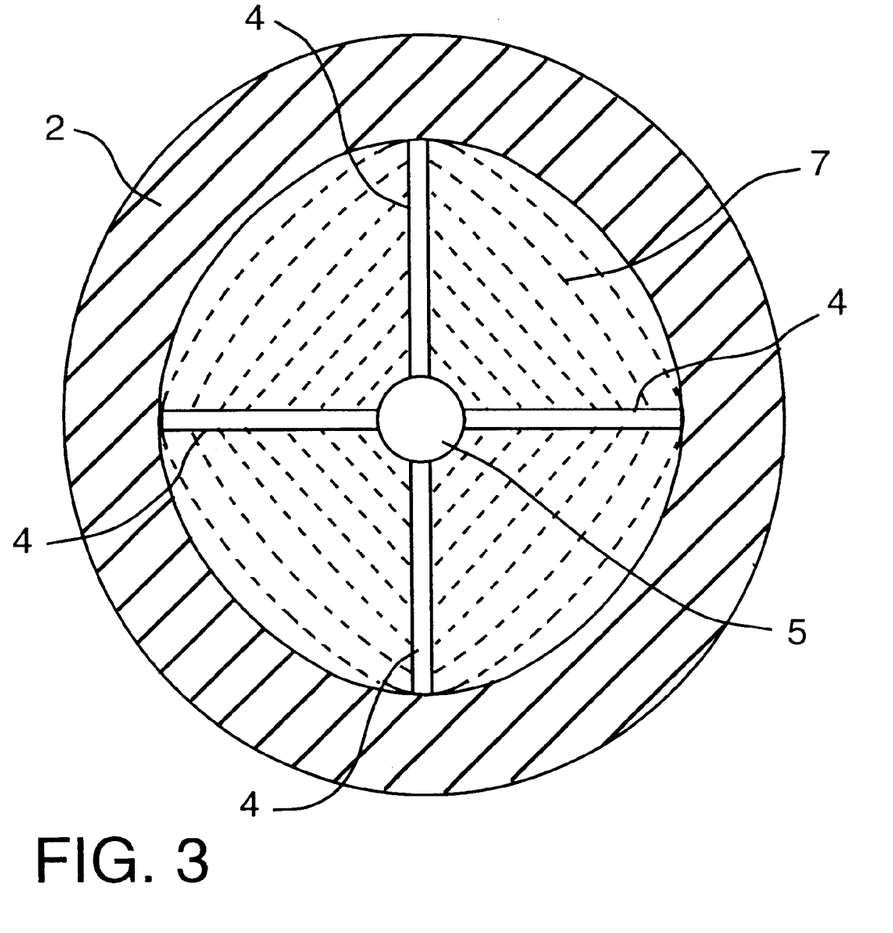
FIG. 3 is an end view of the extended filter of FIG. 1.

When the filter is expanded as illustrated in FIGS. 1 and 2, its outer diameter is preferably less than its length as measured in the axial direction of the guidewire 1 from the point at which the ribs 4 begin to separate from the guidewire 1. In a particularly preferred embodiment, the outer diameter of the expanded filter is less than one half or one third of its axial length. In many medium-sized vessels, the ribs 4 and filter 7 may expand to a diameter against the wall of the vessel of from about 4 to 10 mm, often from about 6 to 8 mm. In larger vessels such as the aorta, the ribs 4 and filter 7 may expand to a diameter of from about 10 to about 30 mm, often from about 12 to 20 mm.

The filter material 7 is preferably a finely porous mesh capable of trapping particles broken loose from interventional procedures, but coarse enough to allow blood to pass through. Suitable filter materials include porous fabrics, plastics such as PTFE and metals. When metal such as Nitinol memory metal is used as the filter material, it preferably has a low profile and facilitates trackability of the filter during use.

Figure 6A:
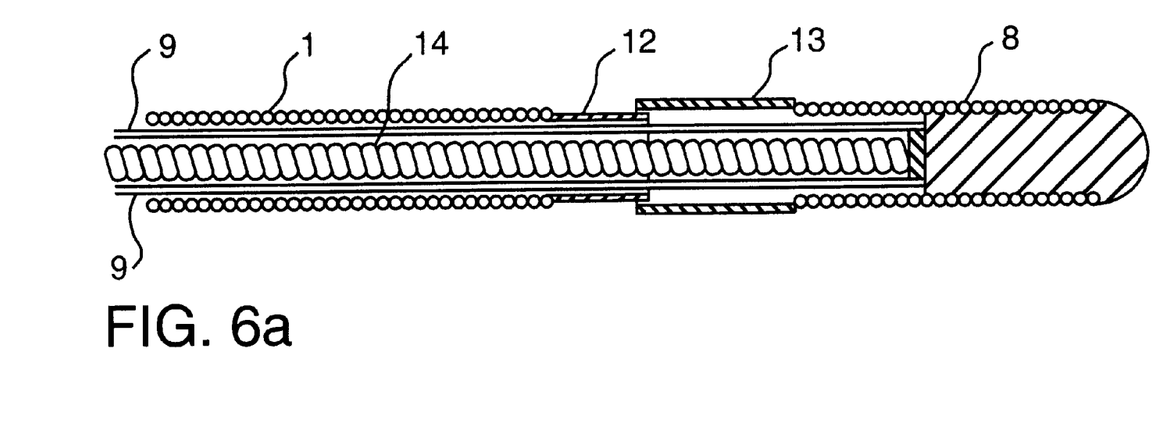
Figure 6B:
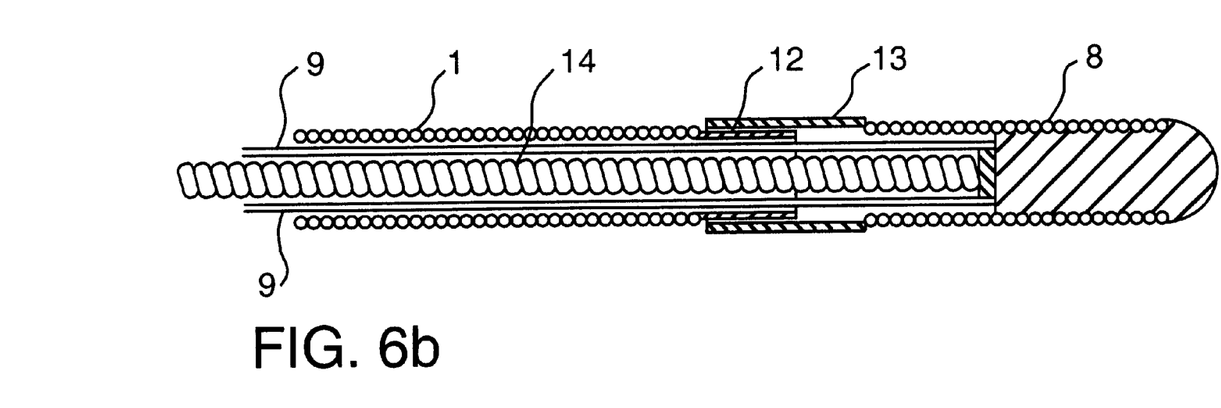

The distal end of the apparatus is inserted past the lesion 15 with the filter 7 in the retracted position. Retraction of the filter 7 is achieved by pulling on the actuator device 8 at the proximal end of the apparatus, as shown in FIG. 6a. Multiple control strings 9 are attached to the actuator 8, run inside the guidewire 1, and exit the guidewire 1 through a collar 10 located approximately 1 cm from the location of the ribs and the retracted filter 7. The control strings 9 are threaded through holes 11 in the collar 10, and are secured to the tips 6 of the ribs 4. In addition to providing a means for the control strings 9 to enter the guidewire 1, the collar 10 may also act as a stopper for coaxial catheters and/or devices which are coaxially advanced along the guidewire 1. The control strings 9 travel through the inside of the guidewire 1 past telescoping sleeves 12 and 13.

The control strings 9 may be made of suitable material such as metal wire, sutures or suture-like materials. The diameter of each suture is preferably 0.005 inch or less.

Pulling the actuator 8 results in tension upon the control strings 9, which results in retraction of the ribs 4 and filter 7 against the guidewire 1. Once the apparatus is deployed in the correct position, the actuator 8 is pushed forward, releasing tension upon the control strings 9 and allowing the ribs 4 and attached filter 7 to self-expand. Similarly, when the procedure is complete, tension along the control strings 9 retracts the ribs 4 and filter 7, allowing the particles and thromboemboli to be retained in a deep pocket formed in the filter material 7. This allows for safe removal of the particles as the apparatus exits the body.

As shown in FIG. 2, a core wire 14 or other type of support member such as tubing may optionally be located inside the guidewire 1 in order to increase structural rigidity of the apparatus while maintaining sufficient flexibility. The core wire may include a tapered tip 19 at its distal end in order to provide increased flexibility at the distal tip 18 of the apparatus. The core wire 14 is connected to the actuator 8 by any suitable means such as soldering, welding or mechanical fasteners. The diameter of the core wire 14 is selected in order to allow sufficient clearance for the control strings between the exterior of the core wire 14 and the interior of the guidewire 1. For example, the core wire 14 or tubing may have an outer diameter of about 0.01 inch. The core wire 14 or tubing may be made of any suitable material such as straight or coiled metal wire or plastic.

Whereas a particular embodiment of this invention has been described above for purposes of illustration, it will be evident to those skilled in the art that numerous variations of the details of the present invention may be made without departing from the invention as defined in the appended claims.

What is claimed is:

1. Apparatus for capturing and retrieving emboli from a blood vessel, the apparatus comprising:
   a hollow tube having a proximal end and a distal end wherein the distal end is insertable into the vessel;
   a collapsible filter attached to the tube near the distal end, the filter comprising a plurality of ribs resiliently biased outwardly from the tube and extending axially along the tube from the distal end toward the proximal end, and a filter material bridging the ribs, wherein the filter is extendable radially outward from the tube toward a wall of the blood vessel, at least one of the ribs and/or the filter material are located at a radial outermost portion of the filter when the filter is in an extended position and contacts the wall of the blood vessel, thereby trapping stenosis fragments while allowing passage of blood flow, and the filter is retractable radially toward the tube to retain the trapped fragments while the tube is withdrawn from the blood vessel; and
   control strings connected to the ribs and running at least partially inside the tube for extending and retracting the filter.

2. The apparatus of claim 1, wherein the control strings enter the tube through a collar mounted on the tube.

3. The apparatus of claim 2, wherein the collar comprises multiple holes through which the control strings are threaded.

4. The apparatus of claim 3, wherein the collar is substantially cylindrical and the holes are substantially equalangularly spaced around a circumference of the collar.

5. The apparatus of claim 1, further comprising a core inside the tube.

6. The apparatus of claim 5, wherein the control strings are located between an exterior surface of the core and an interior surface of the tube.

7. The apparatus of claim 5, wherein the core comprises a tapered distal tip.

8. The apparatus of claim 5, wherein the core comprises coiled metal wire.

9. The apparatus of claim 1, wherein the tube comprises a guidewire.

10. The apparatus of claim 9, wherein the guidewire comprises coiled metal wire.

11. The apparatus of claim 9, wherein the control strings enter the guidewire through a collar mounted on the guidewire.

12. The apparatus of claim 1, further comprising an actuator at the proximal end of the tube operatively connected to the control strings for extending and retracting the filter.

13. The apparatus of claim 12, wherein the control strings are attached at one end to the ribs and at another end to the actuator.

14. The apparatus of claim 1, wherein the tube has an outer diameter of from about 0.02 to about 0.1 inch.

15. The apparatus of claim 1, wherein the tube comprises a guidewire having an outer diameter of about 0.035 inch and an inner diameter of about 0.022 inch.

16. The apparatus of claim 1, wherein the apparatus comprises at least three of the ribs.

17. The apparatus of claim 1, wherein the ribs extend substantially linearly along the axial direction of the tube when the ribs are retracted.

18. The apparatus of claim 1, wherein the ribs comprise rounded tips.

19. The apparatus of claim 1, wherein the ribs comprise metal.

20. The apparatus of claim 1, wherein the filter material comprises at least one porous material selected from plastics and metals.

21. The apparatus of claim 1, wherein the apparatus comprises at least three of the control strings.

22. The apparatus of claim 1, wherein the control strings comprise sutures.

23. Apparatus for capturing and retrieving emboli from a blood vessel, the apparatus comprising:
   a hollow tube comprising a guidewire and having a proximal end and a distal end wherein the distal end is insertable into the vessel;
   a collapsible filter attached to the tube near the distal end, the filter comprising a plurality of ribs resiliently biased outwardly from the tube and extending axially along the tube from the distal end toward the proximal end, and a filter material bridging the ribs, wherein the filter is extendable radially outward from the tube toward a wall of the blood vessel to trap stenosis fragments while allowing passage of blood flow, and retractable radially toward the tube to retain the trapped fragments while the tube is withdrawn from the blood vessels; and
   control strings connected to the ribs and running at least partially inside the guidewire for extending and retracting the filter, wherein the control strings enter the guidewire through a collar mounted on the guidewire.

24. Apparatus for capturing and retrieving emboli from a blood vessel, the apparatus comprising:
   a hollow tube having a proximal end and a distal end wherein the distal end is insertable into the vessel;
   a collapsible filter attached to the tube near the distal end, the filter comprising a plurality of ribs resiliently biased outwardly from the tube and extending axially along the tube from the distal end toward the proximal end, and a filter material bridging the ribs, wherein the filter is extendable radially outward from the tube toward a wall of the blood vessel to trap stenosis fragments while allowing passage of blood flow, and retractable radially toward the tube to retain the trapped fragments while the tube is withdrawn from the blood vessels; and
   control strings connected to the ribs and running at least partially inside the tube for extending and retracting the filter, wherein the control strings enter the tube through a collar mounted on the tube.

25. Apparatus for capturing and retrieving emboli from a blood vessel, the apparatus comprising:
   a hollow tube having a proximal end and a distal end wherein the distal end is insertable into the vessel;
   a collapsible filter attached to the tube near the distal end, the filter comprising a plurality of ribs resiliently biased outwardly from the tube and extending axially along the tube from the distal end toward the proximal end, wherein the ribs comprise rounded tips, and a filter material bridging the ribs, wherein the filter is extendable radially outward from the tube toward a wall of the blood vessel to trap stenosis fragments while allowing passage of blood flow, and retractable radially toward the tube to retain the trapped fragments while the tube is withdrawn from the blood vessels; and control strings connected to the ribs and running at least partially inside the tube for extending and retracting the filter.

* * * * *